(12) United States Patent
Palmer et al.

(10) Patent No.: US 7,189,852 B2
(45) Date of Patent: Mar. 13, 2007

(54) SYNTHESIS

(75) Inventors: Richard Michael John Palmer, Kent (GB); Nicholas Leslie Meyers, Suffolk (GB); John Knight, Wantage (GB)

(73) Assignee: Alizyme Therapeutics Limited, Cambridgeshire (GB)

( * ) Notice: Subject to any disclaimer, the term of this patent is extended or adjusted under 35 U.S.C. 154(b) by 106 days.

(21) Appl. No.: 10/884,842

(22) Filed: Jul. 2, 2004

(65) Prior Publication Data

US 2005/0049416 A1 Mar. 3, 2005

(51) Int. Cl.
*C07D 221/02* (2006.01)

(52) U.S. Cl. ...................... 546/112; 514/299
(58) Field of Classification Search .............. 546/112; 514/299
See application file for complete search history.

(56) References Cited

FOREIGN PATENT DOCUMENTS

| EP | 0 094 742 | 11/1983 |
|----|-----------|---------|
| EP | 0 227 215 | 7/1987 |
| EP | 0 239 321 | 9/1987 |
| EP | 0 454 121 | 11/1991 |
| EP | 0 749 966 | 12/1996 |
| GB | 1 353 331 | 5/1974 |

OTHER PUBLICATIONS

Becker, et al., "Synthetic Strategies for the Construction of Enantiometric Azanoradamantanes", *Tetrahedron*, 53(1): 1-20, 1997.
Hilgetag, et al., "Organisch-Chemische Experimentierkunst", 4th Edition, 246-256, 1970.
King, et al., "Substituted Benzamides with Conformationally Restricted Side Chains. 5. Azabicyclo [x.y.z] Derivatives at 5-$HT_4$ Receptor Agonists and Gastric Motility Stimulants", *J. Med. Chem.* 36: 683-689, 1993.
International Search Report issued for corresponding PCT application PCT/GB2004/003820.

*Primary Examiner*—Amelia A. Owens
(74) *Attorney, Agent, or Firm*—Andrea L. C. Robidoux; Choate, Hall & Stewart LLP

(57) ABSTRACT

The present invention provides an improved process for the production of [(±)-endo]-4-amino-5-chloro-2-methoxy-N-(1-azabicyclo[3.3.1]non-4-yl)benzamide hydrochloride, compositions thereof, and intermediates thereto.

10 Claims, No Drawings

SYNTHESIS

CROSS REFERENCE TO RELATED APPLICATIONS

This application claims priority, under 35 U.S.C. §119 (a), to Patent Application serial number GB 0321091.1 filed Sep. 9, 2003, the contents of which are incorporated herein by reference.

The present invention provides an improved process for the production of [(±)-endo]-4-amino-5-chloro-2-methoxy-N-(1-azabicyclo[3.3.1]non-4-yl)benzamide hydrochloride, and intermediates thereof.

EP-A-94742 discloses a class of substituted azabicyclo compounds having dopamine antagonist activity, useful in the treatment of disorders relating to impaired gastro-intestinal motility, such as retarded gastric emptying, dyspepsia, flatulence, oesophageal reflux, and peptic ulcer. EP-A-94742 further discloses the use of these compounds in the treatment of emesis, disorders relating to impaired gastro-intestinal motility or disorders of the central nervous system.

Example 9 of EP-A-94742 discloses the compound (±)-4-amino-5-chloro-2-methoxy-N-(1-azabicyclo[3.3.1]non-4-yl)benzamide known by the generic name renzapride.

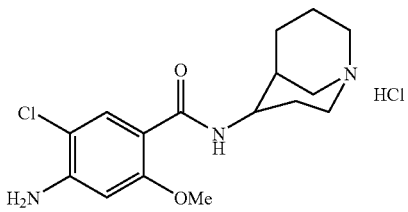

The hydrochloride salt of renzapride (renzapride hydrochloride) as illustrated above is preferred over the free base because of its improved stability.

EP-A-0239321 discloses a hydrated form of the hydrochloride salt of renzapride, which exists in crystalline form and provides improved handling and stability characteristics over the anhydrous hydrochloride salt of renzapride.

EP-A-94742 discusses general procedures for the formation of compounds of formula I

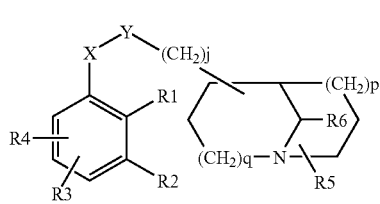

(I)

which involve reacting a compound of formula (XVIII) with a compound of formula (XIX) as illustrated below,

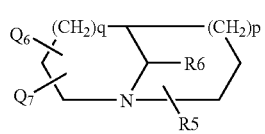

(XVIII)

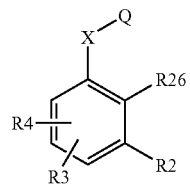

(XIX)

wherein Q is a halogen, $Q_6$ is $NH_2$ and $Q_7$ is H, in an inert non-hydroxylic solvent at non-extreme temperatures in the presence of an organic or inorganic base. The production of (±) 4-amino-5-chloro-2-methoxy-N(4'[1'-azabicyclo[3,3,1]-nonyl-benzamide is set out in examples 8 and 9 of EP-A-94742.

U.S. Pat. No. 4,857,647 discloses a process for the preparation of an acid chloride of formula (XIX) from the corresponding acid using thionyl chloride.

U.S. Pat. No. 4,697,019 discloses N-(heterocyclic substituted) benzamides and their production. U.S. Pat. No. 4,697,019 discloses a process for the preparation of an amine from a ketone functionality by initially converting the ketone to an oxime using hydroxylamine hydrochloride. The oxime is then reduced using lithium aluminium hydride in tetrahydrofuran (THF) or using catalytic hydrogenation.

The present invention provides a process for the production of renzapride and its hydrochloride and hydrochloride hydrate. The process allows the production of renzapride on a laboratory or industrial scale. Renzapride can therefore be provided in quantities, which are suitable for therapeutic and/or experimental use. In particular, the process of the present invention can provide renzapride at a level of 5 kg or above for experimental use or at a level of 100 kg or above for industrial or commercial use. The present invention further provides an improved process for the production of important intermediates in the synthesis of renzapride.

The first aspect of the present invention provides a process for the preparation of compound (8)

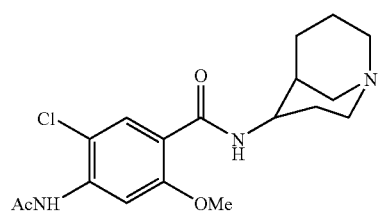

(8)

comprising preparing acid chloride (13) from acid (11)

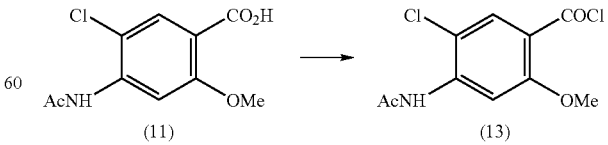

using an activating agent such as oxalyl chloride or thionyl chloride in a solvent selected from dichloromethane, toluene, dimethylformamide (DMF) or tetrahydrofuran (THF), reacting the acid chloride (13) in toluene with amine (14)

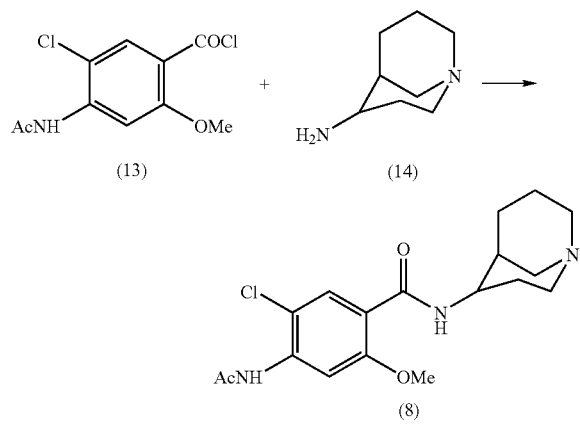

(8)

and isolating the product (8) therefrom.

Preferably, the formation of the acid chloride is carried out by reacting acid (11) with DMF and thionyl chloride in the presence of THF, wherein the DMF is added to the acid (11) prior to the thionyl chloride. The acid chloride (13) is removed by filtration.

The preparation of the acid chloride (13) is preferably carried out in THF. This solvent allows good conversion of the acid (11) to the acid chloride (13) (greater than 80% conversion). In addition, the resulting acid chloride (13) is insoluble in the reaction mixture and can therefore be easily isolated, for example by filtration. Preferably, the volume of solvent is 1 to 10 volumes, preferably 1 to 6 volumes, more preferably 2 volumes or above in order to ensure a more mobile slurry and prevent agitation problems. For the purposes of the present invention, the term 'volume' relates to the amount of solvent added to the components of the reaction mixture and is determined in relation to a component of the reaction mixture. Thus, if the component of the reaction vessel present at level of 10 kg is designated as 1.0 wt, then 5 volumes of solvent will require the addition of 50 liters of solvent to the reaction vessel.

The addition of DMF to the acid prior to the addition of the thionyl chloride allows rapid reaction of the thionyl chloride and affords better temperature control. DMF is added in catalytic amounts for example 0.01% by weight, in order to activate the thionyl chloride.

Preferably, after reaction to form the acid chloride, a solvent exchange is carried out with toluene. This toluene solvent exchange is preferably carried out at reduced pressure with the internal temperature being less than 30° C. The use of the solvent exchange reduces the levels of acidic by-products from the thionyl chloride and the solvent in the acid chloride prior to coupling.

The coupling reaction is carried out in toluene thus allowing the telescoping of the two steps of producing the acid chloride and carrying out the coupling reaction.

For the purposes of this invention, telescoping of reaction steps is the practice of joining together consecutive reaction steps and avoiding isolation of the compounds produced by each reaction step. The telescoping of reaction steps can save significant plant time and can achieve significant economic savings in solvents. Moreover, this practice is advantageous when the produced compounds are hazardous or labile or where the produced compounds are not solids and are more difficult to isolate. Telescoping of reaction steps avoids the need for procedures such as evaporation of a reaction mixture to a residue, which can be time consuming and impractical on a larger scale.

The coupling step may optionally be carried out in the presence of an inorganic or organic base such as triethylamine. The coupling reaction may optionally be carried out at room temperature or may be heated to 50° C. or above.

The coupling of the acid chloride (13) to the amine (14) establishes the renzapride structure. Optimisation of this coupling step by the selection of solvents or order of reagent addition allows the provision of renzapride in greater quantities. The provision of renzapride on a larger scale allows the therapeutic use of renzapride.

In particular, the telescoping of the acid chloride formation and the coupling steps provides a process which is amenable to industrial scale use. The process of the first aspect allows the production of the amide (8) without the need for isolation of the acid chloride (13). Such a simplified process is more useful for the commercial production of renzapride. For the purposes of the present invention, laboratory scale production means synthesis of renzapride hydrochloride hydrate from approximately 0.1 to approximately 10 kg and industrial scale production provides renzapride hydrochloride hydrate at approximately 100 kg or above, preferably from approximately 10 to approximately 200 kg.

In an alternative feature of the first aspect, the formation of the acid chloride and the condensation reaction can be carried out in one step, wherein the acid (11) is dissolved in dimethylformamide and triethylamine is added. Ethyl chloroformate is added to the solution to form an activated acyl unit, such as the acid chloride (13) followed by the addition of toluene and a solution of amine (14) in toluene.

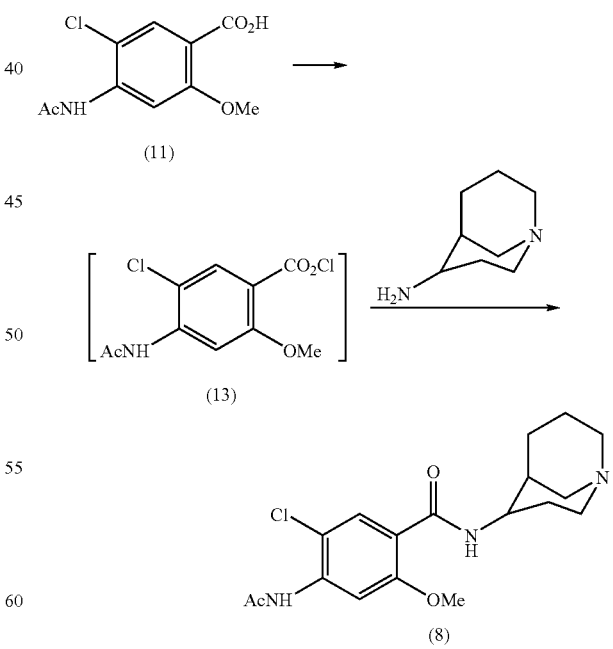

The second aspect of the invention provides a process for the production of a compound (9) comprising producing an activated acyl unit, such as acid chloride in situ from the acid (16) and reacting said acid chloride with an amine (14).

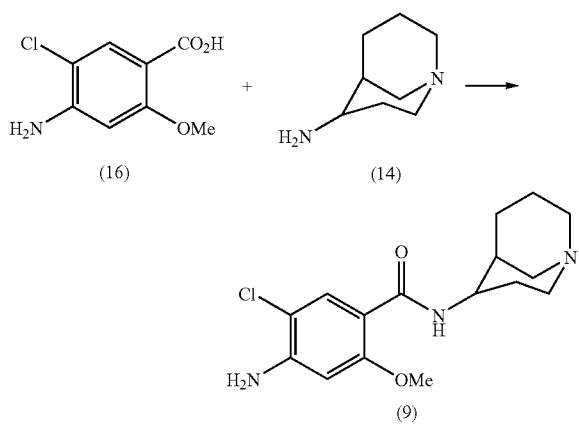

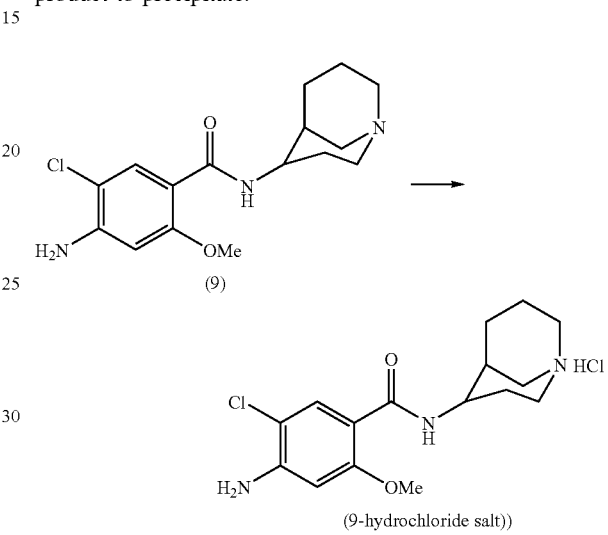

Generation of the corresponding activated acyl unit, for example the acid chloride occurs in situ followed by condensation with amine (14). The acid (16) is dissolved in dimethylformamide and triethylamine is added. Ethyl chloroformate is added to form the activated acyl unit (for example an acid chloride) followed by toluene and a solution of amine (14) in toluene. The resulting amide (9) precipitates from the reaction mixture and can be isolated by filtration.

This "one pot" synthesis provides a direct synthesis of renzapride from amine (14) and acid (16) and avoids the need for protection at the phenylamine. Such synthesis allows the production of renzapride in fewer synthetic steps thereby providing a synthetic route amenable to industrial scale up.

The third aspect of the invention provides a process for the preparation of renzapride from compound (8) comprising preparing compound (9) from compound (8)

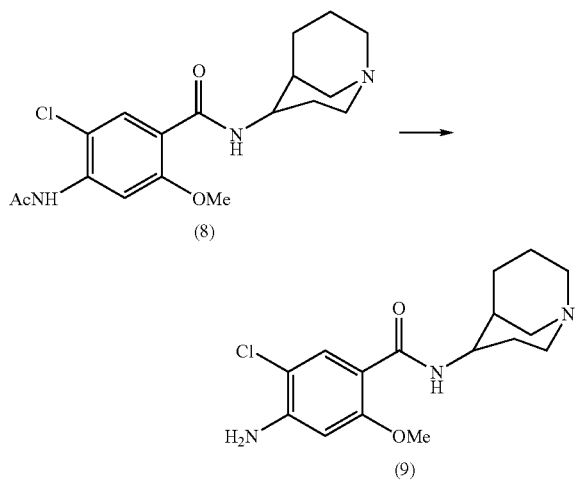

by refluxing compound (8) with a compound NaOR wherein R is hydrogen methyl or ethyl, preferably methyl, and methanol or ethanol;

The base mediated hydrolysis of the acyl protected amine may be carried out using sodium hydroxide in an ethanol/water mixture or methanolic sodium methoxide at reflux. Conditions such as sodium hydroxide in ethanol/water have to be used with care as they have been shown not to be compatible with glass-lined vessels. The use of sodium methoxide in methanol at reflux allows comparable conversion to the de-protected amine and provides the use of reaction conditions which are compatible with glass. Such reaction conditions allow the de-protection reaction to be carried out using conventional reaction vessels and thus allow scale up of this step without requiring the use of steel or alloy vessels.

The formation of the hydrochloride salt of compound (a) is carried out in accordance with EP 0239321 wherein a compound of formula (a) is dissolved in a suitable solvent, preferably ethanol, and a solution of hydrochloric acid in a suitable solvent, preferably ethanol, is added, allowing the product to precipitate.

Formation of the hydrate of renzapride hydrochloride can be carried out by placing the renzapride hydrochloride on a tray over water in a closed vessel for 36 hours as set out in EP 0239321.

Prior to salt formation, a solution of renzapride in ethanol is preferably clarified hot through a filter. Clarification should preferably be carried out between 40° C. and 65° C., more preferably between 45° C. and 60° C. Clarification can be carried out through conventional media such as celite, but clarification through filter or glass microfibre paper has been found to be sufficient.

The fourth aspect of the invention provides a process for the preparation of compound (14) from compound (7) comprising decomplexation of the tertiary amine of compound (7) to produce compound (14)

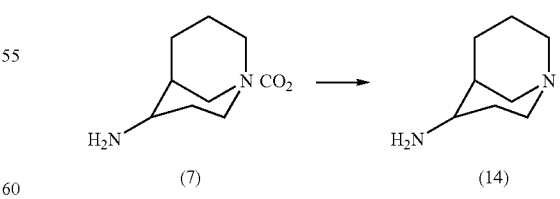

by reflux in toluene followed by azeotropic drying of the produced compound (14) in solution.

The de-complexation of the amine (7) is achieved by refluxing the amine (7) in toluene. The solvent volumes for the de-complexation are 1 to 10 volumes, preferably 1 to 6 volumes, more preferably 2 volumes or above. The increase in solvent volumes allows improved agitation of the initial slurry.

Filtration of the de-complexed amine solution allows the removal of any inorganic material present from the formation and reduction of the oxime. This filtration step improves the yield of any subsequent coupling reaction by removing impurities from the reaction mixture. In addition, the filtration step also removes any complexed amine (7) as the amine complex is insoluble in toluene.

Amine (14) is a key intermediate in the formation of renzapride. The fourth aspect provides an improved process for the synthesis of amine (14) which is amenable to industrial scale-up.

The fifth aspect of the invention provides a process for the formation of a compound of formula (7) comprising

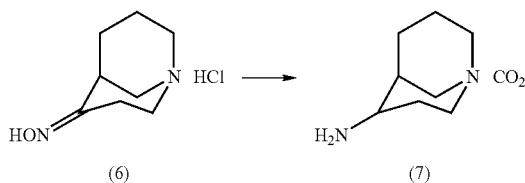

reacting compound (6) with sodium followed by reaction with carbon dioxide characterised in that the reaction is carried out in butanol.

The oxime (6) is reduced to produce the amine (7) by the addition of sodium in n-butanol. The use of n-butanol allows better control over the reaction exotherm. In addition, as both the formation of the oxime and the reduction of the oxime to form the amine are carried out in butanol, the formation and reduction steps can be telescoped. This allows these steps to be carried out with greater efficiency. Furthermore, the use of n-butanol as the solvent provides a significantly improved yield (i.e. 73–96%) compared with the yield obtained using ethanol (50–60%).

Crystallisation of the complexed amine can be achieved by the addition of water to the solution of the complexed amine in butanol. Isolation of the crystallised complexed amine can then be achieved by filtration.

The sixth aspect of the invention relates to a compound of formula (7)

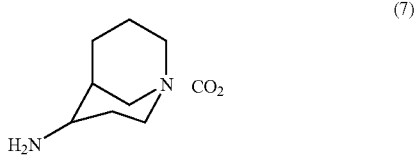

The seventh aspect of the invention relates to a process for the formation of an oxime (6) comprising

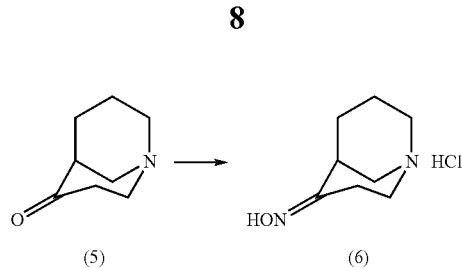

reaction of compound (5) with hydroxylamine in ethanol or butanol.

The production of the oxime (6) is carried out by incubation of the ketone (5) with solid hydroxylamine hydrochloride in solvent. The controlled addition of a solid to a reaction is difficult and undesirable especially if accompanied by an exotherm. The seventh aspect of the invention therefore preferably involves the use of a reverse addition procedure involving the addition of a solution of the ketone (5) to a slurry of hydroxylamine hydrochloride in n-butanol. This process allows easier and safer handling and avoids problems associated with the controlled addition of solids.

The invention preferably provides a process for the formation of a compound of formula (14) from a compound of formula (5) comprising conversion of a compound of formula (5) into a compound of formula (6) by the process of the seventh aspect, conversion of a compound of formula (6) into a compound of formula (7) by the process of the fifth aspect and decomplexation of the compound of formula (7) to form a compound of formula (14) by the process of the fourth aspect.

The eighth aspect of the invention provides a process for the preparation of compound (5) from ethyl nipecotate comprising production of compound (3)

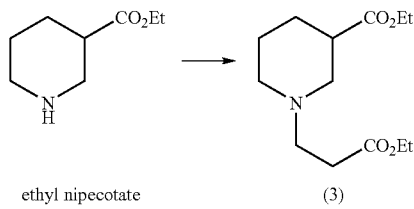

by reaction of ethyl nipecotate with ethyl acrylate; production of compound (4) from compound (3)

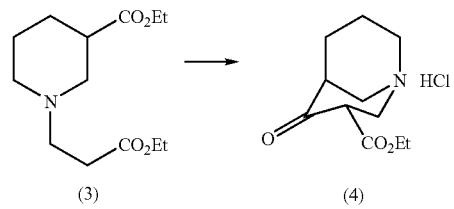

by reflux of compound (3) with base and formation of compound (5) from compound (4)

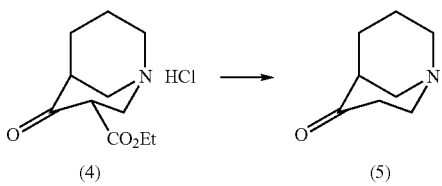

(4)  (5)

by reaction of compound (4) with aqueous HCl followed by sodium hydroxide.

Preferably, the reaction of ethyl nipecotate with ethyl acrylate is carried out in toluene. The use of toluene provides means for better control over any resulting exothermic reaction. In addition, the product (3) is produced in solution and can be carried directly into the production of compound (4). The use of solvent and the ability to carry through the reaction product (3) into the subsequent reaction allows the usual work up of compound (3) to be eliminated with no loss of yield or quality.

Production of compound (4) is also preferably carried out in toluene in the presence of a base such as sodium hydride or potassium tert-butoxide (tBu-OK), more preferably tBu-OK. The reaction is quenched with water and the aqueous phase is acidified to approximately pH-1 by the addition of concentrated hydrochloric acid. This acid aqueous solution can then be used directly in the subsequent reaction to produce compound (5). The production of the nor-adamantanone (5) is carried out by refluxing the acidic aqueous solution containing compound (4) and then extracting the product (5) with n-butanol. The use of n-butanol as the extraction solvent allows the solution to be used directly in the formation of the oxime (6) as discussed in the seventh aspect of the invention, thereby providing a more efficient synthesis of both compound (5) and the subsequent oxime (6).

The ninth aspect of the invention relates to a process for the preparation of acid (11) from compound (10)

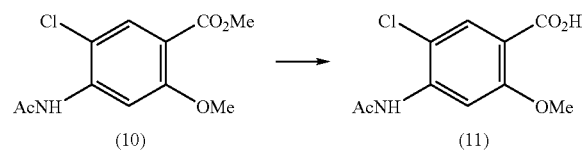

(10)  (11)

by the addition of aqueous sodium hydroxide to a slurry of compound (10) in water, followed by precipitation of acid (11) by the addition of hydrochloric acid.

The ninth aspect of the invention involves a recrystallisation procedure. This procedure allows better control of dimer impurities which may be formed on de-protection of the ester to the free acid.

The tenth aspect of the invention relates to a process for the preparation of acid (16) from compound (10). Compound (10) is incubated with aqueous potassium hydroxide and ethanol, followed by the addition of hydrochloric acid to produce the acid (16). The acid (16) may be provided as the hydrochloric salt.

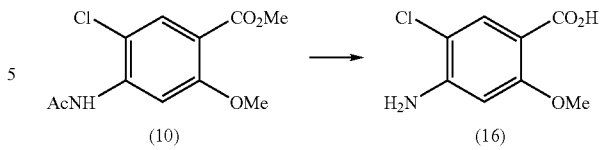

(10)  (16)

The eleventh aspect provides a process for the preparation of amine (14) comprising the steps of a) preparing ketone (5) as set out in the eighth aspect of the invention and b) converting the ketone (5) into amine (14) as set out in the seventh, fifth and fourth aspects of the invention.

All preferred features of the fourth, fifth, seventh and eighth aspects of the invention also relate to the eleventh aspect.

The twelfth aspect of the invention provides a process for the preparation of compound (8) comprising a) forming amine (14) as set out in the eleventh aspect of the invention and b) reacting amine (14) with acid (11) as set out in the first aspect of the invention.

All preferred features of the eleventh and first aspects of the invention also relate to the twelfth aspect.

The thirteenth aspect of the invention provides a process for the preparation of compound (8) comprising a) forming amine (14) as set out in the eleventh aspect of the invention and b) forming acid (11) from acid (10) as set out in the tenth aspect and c) reacting the acid (11) with the amine (14) as set out in the first aspect of the invention.

All preferred features of the first, tenth and eleventh aspects of the invention also relate to the thirteenth aspect.

The fourteenth aspect of the invention provides a process for the preparation of compound (9) comprising preparing compound (9) from compound (8) prepared according to the twelfth or thirteenth aspects, as set out in the third aspect of the invention.

All preferred features of the third, twelfth or thirteenth of the invention also apply to the fourteenth aspect.

The fifteenth aspect of the invention provides a process for the formation of compound (9) comprising reacting amine (14) as provided by the eleventh aspect with acid (16) as set out in the second aspect of the present invention.

All preferred features of the second and eleventh aspects of the invention also apply to the fifteenth aspect.

The sixteenth aspect of the invention provides a process for the formation of compound (9) comprising a) forming acid (16) from compound (10) as set out in the tenth aspect and b) forming amine (14) as set out in the eleventh aspect and c) reacting amine (14) with acid (16) as set out in the second aspect of the invention.

All preferred features of the second, tenth and eleventh aspects of the invention, also apply to the thirteenth aspect.

The seventeenth aspect of the invention provides a process for the formation of the hydrochloride of compound (9) as produced by the fourteenth, fifteenth or sixteenth aspects comprising reacting compound (9) with ethanolic hydrochloric acid.

All preferred features of the fourteenth, fifteenth or sixteenth aspects also apply to the seventeenth aspect.

The eighteenth aspect of the invention provides a process for the production of renzapride hydrochloride comprising
  reacting ethyl nipecotate with ethyl acrylate in toluene;
  reacting the resulting solution with tBuOK extracting the resulting compound in water and acidifying the aqueous solution;

refluxing the aqueous solution with hydrochloric acid and extracting the resulting product into butanol;

carrying out the reversed addition of the butanol solution to a slurry of hydroxylamine hydrochloride to form an oxime;

reacting the oxime in butanol with sodium followed by reaction with carbon dioxide to form a complexed amine;

de-complexation of the amine by reflux in toluene;

reaction of the de-complexed amine with acid chloride (13) and isolating the product therefrom;

de-protecting the acyl protected amine by reflux with methanolic sodium methoxide and finally producing the hydrochloride salt by the addition of ethanolic hydrochloric acid.

The nineteenth aspect relates to compounds as produced by the process of the first to eighteenth aspects of the invention.

The twentieth aspect of the invention relates to a pharmaceutical composition comprising a compound of formula (9) or a hydrochloride salt thereof as produced by the process of the first to nineteenth aspects of the invention, and a pharmaceutical excipient.

Suitable carriers and/or diluents are well known in the art and include pharmaceutical grade starch, mannitol, lactose, magnesium stearate, sodium saccharin, talcum, cellulose, glucose, sucrose (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The compounds according to the invention for use in the aforementioned indications may be administered by any convenient method, for example by oral (including by inhalation), parenteral, mucosal (e.g. buccal, sublingual, nasal), vaginal, rectal or transdermal administration and the compositions adapted accordingly.

For oral administration, the compounds can be formulated as liquids or solids, for example solutions, syrups, suspensions, emulsions, tablets, capsules, lozenges, dry powder and/or granules.

A liquid formulation will generally consist of a suspension or solution of the compound or physiologically acceptable salt in a suitable aqueous or non-aqueous liquid carrier(s) for example water, ethanol, glycerol, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous carrier or non-aqueous or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels and patches, and injections, including powder injections.

Conveniently the composition is in unit dose form such as a tablet, capsule or ampoule.

The compositions may contain from 0.1% to 99% (w/w) preferably from 0.1–60% (w/w), more preferably 0.2–12% by weight and most preferably 0.25 to 8% (w/w) of the renzapride or the hydrochloride, or hydrochloride hydrate, depending on the method of administration.

In particular the seventeenth aspect relates to a pharmaceutical composition for oral administration. The composition is preferably provided as a tablet or capsule and the excipient is preferably starch.

The eighteenth aspect of the invention relates to a method of treating a disorder relating to impaired gastro-intestinal motility comprising administering to a subject in need thereof a compound of formula (9) or the hydrochloride salt thereof. For the purposes of the present invention, gastrointestinal includes the oesophagus, the stomach, the small intestine and the large intestine (including the colon and the rectum). Renzapride may generally be used in the treatment of disorders relating to impaired gastro-intestinal motility. The disorders include one or more of irritable bowel syndrome, retarded or delayed gastric emptying, dyspepsia, oesophageal reflux, peptic ulcer, flatulence, impaired evacuation, constipation, diabetic neuropathy, functional abdominal bloating or abdominal pain. Renzapride can also be used in the treatment of symptoms associated with such disorders including abdominal pain and/or discomfort, abdominal bloating, an abnormality in stool consistency, an abnormality in frequency of stool passage, a feeling of incomplete emptying, feelings of urgency and passage of mucus. It may also be used in the treatment of emesis and/or the treatment of disorders of the central nervous system such as psychosis. Preferably renzapride is used for the treatment of irritable bowel syndrome, more preferably constipation-predominant or alternating (mixed-symptom) irritable bowel syndrome.

The amount of renzapride effective to treat a disorder as set out above depends on the nature and severity of the disorder being treated and the weight of the patient in need thereof. However, a single unit dose for a 70 kg adult will normally contain 0.01 to 100 mg, for example 0.1 to 50 mg, preferably 0.5 to 6 mg of the compound of the invention per day. Unit doses may be administered once or more than once a day, for example, 2, 3 or 4 times a day, usually 1 to 3 times a day, more preferably 1 or 2 times per day. The total daily dosage can be in range of approximately 0.0001 to 0.2 mg per kg per day, more usually 0.001 to 0.1 mg per kg per day, preferably 0.01 to 0.1 mg per kg per day. The unit dose is preferably provided in the form of a capsule or a tablet.

The present invention will now be illustrated by reference to the following non-limiting examples:

EXAMPLES

Scheme A

Stage One

A reaction vessel is charged with ethyl nipecotate (1.0 wt, 0.99 vol, 1.0 mol eq) followed by toluene (1.0 vol, 0.86 wt). The temperature of the resulting solution is then adjusted to 18–23° C. Ethyl acrylate (1.03 mol eq, 0.71 vol, 0.66 wt) is charged over 40–50 minutes maintaining the temperature at less than 45° C. Toluene (0.5 vol, 0.43 wt) is then charged over 15–20 minutes. The reaction is sampled and then the temperature increased to 48–52° C. until the reaction is complete (<2% starting material by GC). The reaction is expected to take 12 hours however, the reaction is stable for at least 48 hours. After the reaction is complete a sample is removed for $^1$H NMR in order to establish the residual level of ethyl acrylate.

The reaction mixture is then charged with toluene (1.0 vol, 0.86 wt) which is then removed by vacuum distillation at a temperature of 40–52° C. A further charge of toluene (1.0 vol, 0.86 wt) is added and distilled as before and then a sample of reaction mixture is removed for $^1$H NMR (pass <0.2% w/w ethyl acrylate).

The resultant yellow/green solution, which can be stored at room temperature for at least 2 weeks, is then used directly in stage 2.

The final solution concentration is expected to be ca 60% (w/w), as determined by $^1$H NMR. Yield is 160% (w/w); 97.6% th.

Stage Two

A reaction vessel is charged with potassium tert-butoxide (0.87 wt, 2.0 mol eq) and toluene (10.8 wt, 12.5 vol) and the mixture heated to reflux (108 to 111° C.). The product of stage 1 (1.00 wt, 1.0 mol eq) as a solution in toluene (ca 1.7 vol total) is added to the reaction vessel, maintaining the internal temperature at 108 to 111° C. A line rinse of toluene (1.3 wt, 1.5 vol) is added, maintaining the internal temperature at 108 to 111° C., then the mixture stirred at reflux until reaction is complete by GC (approx. 2 hours, <0.03% (w/w) starting material by GC).

The mixture is cooled to 5 to 10° C. over 2 to 3 hours and then quenched with purified water (5.0 vol) maintaining the internal temperature at ≦15° C. The temperature of the mixture is adjusted to 20 to 25° C. and the phases separated. The pH of the aqueous phase is checked (expected to be 14) and the phase cooled to 5 to 10° C. over 30 to 60 minutes. The pH is adjusted to 8 to 9 with conc. hydrochloric acid (0.56 to 0.62 wt, 0.47 to 0.52 vol, expected) maintaining the internal temperature at ≦25° C. The aqueous solution is sampled for yield/purity determination, then acidified to pH 1 by addition of further conc. hydrochloric acid (0.56 to 0.62 wt, 0.47 to 0.52 vol, expected) maintaining the internal temperature at ≦25° C.

The pale orange aqueous solution is then carried forward to stage 3.

Yield is 62.2% (w/w), 64.5% th.

Stage Three

A reaction vessel is charged with acidic aqueous solution of stage 2. Concentrated hydrochloric acid (3.76 wt, 3.13 vol, based on amount of contained stage 2 product), is added to the solution keeping the temperature below 35° C. The addition is expected to take 30–45 minutes. The vessel contents are heated to 100 to 105° C. over 90–120 minutes, while distilling out volatile impurities (approximately 0.7–0.8 vol). The temperature is maintained at reflux (≧100° C.) and the reaction is monitored by TLC. The reaction is deemed complete when stage 2 product is absent when compared with a reference standard. The reaction is expected to take 12–16 hours.

When reaction is complete, the solution is cooled to 5 to 10° C. over 2 to 3 hours and the pH adjusted to 11.5 to 12.5 with 40% (w/v) aq NaOH solution (ca 5.13 vol), maintaining the internal temperature at ≦15° C., over a period of 2–3 hours. If the pH range is exceeded, it should be brought back into range with the addition of aqueous HCl.

The aqueous layer is adjusted 30–35° C., extracted with n-butanol (4×5.27 wt, 4×6.5 vol) and the organic layers combined. The aqueous layer is checked for presence of product by TLC, and re-extracted with n-butanol if required. The combined organic solution is concentrated to ca. 4 vol under vacuum, keeping the temperature at 40 to 50° C. The water content of the organic phase is determined by the Karl Fischer Water Determination method (KF), if the result is >0.2% (w/w) further n-butanol (4.05 wt, 5.0 vol) is added, and distilled under vacuum at 40–50° C., and the solution is re-analysed for water content.

The yield of stage 3 is determined by GC (w/w) assay, and the solution of stage 3 in n-butanol carried through to the stage 4 reaction.

Yield 52.0% (w/w), 91.9% th.

Stage Four

A solution of the product of stage 3 (1.0 wt, 1.0 mol eq) in n-butanol (volume varies) is concentrated to ca 4 vol by vacuum distillation, maintaining the temperature below 50° C.

A reaction vessel is charged with hydroxylamine hydrochloride (0.55 wt, 1.1 mol eq) and n-butanol (3.0 vol. 2.43 wt). The concentrated renzapride stage 3 solution is charged to the hydroxylamine hydrochloride/n-butanol mixture, maintaining the temperature between 20 and 30° C. (the addition is expected to take 0.5 to 1 hour), followed by a line rinse of n-butanol (1.0 vol, 0.81 wt). The reaction is stirred at 20–25° C. and monitored by GC (pass result is <1% area SM; expected to take up to 12 hours).

The reaction mixture is then cooled to 5–10° C. and aged for at least 2 hours until precipitation is judged complete. If after 8 hours the precipitation is not complete, the reaction mixture is cooled to 0–2° C. and stirred for up to 72 hours to reach maximal precipitation.

The solid is then collected by filtration, and the filter cake washed with cold (<10° C.) n-butanol (1.62 wt, 2.0 vol). Note the product is markedly hygroscopic; protect from moisture.

The filter cake is then transferred to a vacuum oven and dried at up to 40° C. until constant weight is obtained (expected drying time 18–24 hours).

Yield 91.0 th, 125.0% (w/w).

Stage Five

The product of stage 4 (1.0 wt, 1.0 mol eq) is charged to a reaction vessel followed by n-butanol (11.34 wt, 14.0 vol) and the stirred slurry heated to 90–95° C. Heating is stopped, and sodium metal (0.81 wt, 6.75 mol eq) is added portionwise via the solid addition port, maintaining the temperature at 90–130° C. As necessary, the jackets should be adjusted to prevent the reaction temperature falling below 90° C. The addition is expected to take 1.5–2.5 hours.

The reaction is then monitored by GC (pass result is <2% area starting material; expected to be complete by end of sodium addition). Further sodium (0.1 wt) is added if the reaction has not gone to completion.

The reaction mixture is quenched by the addition of purified water (6.0 vol), maintaining the temperature at 50–130° C. The addition is expected to take 15–30 minutes. The reaction is then cooled to 20–25° C. The two phases are separated and the organic phase washed with a 10% (w/v) brine solution (2×2.0 vol). The organic phase is concentrated to ca 9 vol, at atmospheric pressure, by the removal of ca 15 vol of distillate and the concurrent addition of n-butanol (8.1 wt, 10.0 vol).

The reaction is cooled to 20–25° C. and then clarified to remove inorganics, and the filter rinsed with n-butanol (0.405 wt, 0.5 vol) and the combined organic solution weighed. The solution is returned to the reactor followed by a line rinse of n-butanol (0.405 wt, 0.5 vol) and the water content adjusted, as necessary, to 4.5–4.9% (w/w) by the addition of purified water (weight based on total weight of solution plus line rinse).

The temperature is adjusted to 30–35° C. and carbon dioxide gas is passed through the solution, maintaining the temperature at 35–45° C. Gas addition is continued until there is no discernible exotherm, and then for an additional 30 minutes.

The slurry is cooled to 0–5° C. and aged at this temperature for 2–3 hours. If precipitation is judged complete, the solid is filtered off and washed with TBME (1.48 wt, 2.0 vol) and dried at up to 40° C. until the n-butanol content is <1% w/w.

Yield 69.5% th, 67.3% (w/w).

Stage Six

Stage Six reaction/purification

A reaction vessel is charged with purified water, (5.0 vol) and the methoxy benzoate from stage 5 (1.00 wt, 1.0 mol eq) is added with stirring. The mixture is stirred at 15 to 25° C. for 20 to 30 minutes then sodium hydroxide solution (0.31 wt in 4.7 wt purified water) is added, maintaining internal temperature at 15 to 25° C. A pH check is performed and should be pH 14. The mixture is then stirred at 20–25° C. until complete dissolution is obtained or when the level of the amino acid impurity reaches 2% by HPLC.

The mixture is cooled to 5 to 10° C., filtered and the solid washed with purified water (2.0 vol). Concentrated hydrochloric acid (1.14 wt, 0.95 vol) is added to the combined filtrates as soon as practicable after completion of the reaction, maintaining the internal temperature at ≦25° C. The pH of the resulting mixture should be <1. The slurry is then cooled to 5 to 10° C. over 1 to 2 hours, stirred for an additional 1 to 2 hours at this temperature, then filtered. The filter cake is washed with purified water (2.0 vol) until the pH of the filter cake, when slurried with water, is >4 (approx 4 washes in total required). The crude product is then dried under vacuum at up to 60° C. until water content is <1% by the Karl Fischer Water Determination method (KF).

The crude product is sieved, then charged to a reaction vessel. IPA (15.7 wt, 20.0 vol) is added and the mixture heated to reflux. Once the solid has dissolved, the mixture is then concentrated to 8.7 vol at 60–80° C. The solution is then cooled to 5 to 10° C. over 1 to 2 hours and the slurry aged for 2 to 3 hours. The solid is collected by filtration and the cake washed with IPA (1.57 wt, 2.0 vol) pre-cooled to 5 to 10° C. The solid is then dried under vacuum at up to 60° C. until IPA is <0.1% (w/w) by $^1$H NMR.

Stage Six Rework Procedure

A reaction vessel is charged with purified water, (3.0 vol) and the methoxy benzoic acid (Code NT/0055, 1.00 wt, 1.0 mol eq) is added with stirring. The mixture is cooled to 5–10° C. and sodium hydroxide solution (0.28 wt in 7.0 wt purified water, ca 6.15 vol required) is added, maintaining internal temperature at 5–10° C. A pH check is performed and should be pH 14. If necessary, further sodium hydroxide solution is added to give pH 14. The mixture should not be left for any length of time as decomposition will occur. Complete dissolution may or may not occur depending on the IPA content of the input material.

Concentrated hydrochloric acid (0.87 wt, 0.74 vol) is added to the reaction, maintaining the internal temperature at ≦15° C. The pH of the resulting mixture should be ≦1. If necessary, additional hydrochloric acid is added to give the correct pH. The mixture will become a thick slurry as the acidification proceeds. The slurry is then cooled to 5 to 10° C. and stirred at this temperature for 60–120 minutes. The solid is filtered and the filter cake is washed with purified water (4×2.0 vol) until the pH of the filter cake, when slurried with water, is >4. Additional washes may be carried out as necessary. The product is then dried on the filter for at least 2 hours then under vacuum at up to 50° C. until water content is <0.1% by KF.

Yield (inclusive of rework procedure) 68.0% (w/w), 71.9% th.

Stage Seven

It is envisaged that the amine de-complexation is carried out first in order that the amount of available amine can be determined ahead of batching the stage 6 acid for acid chloride formation. The de-complexed amine should be held under inert atmosphere with rigorous exclusion of carbon dioxide and water pending acid chloride formation.

Stage 7B: De-Complexation of the Amine-Carbon Dioxide Complex

Stage 5 product (1.00 wt, 1.0 mol eq) is charged to the reactor configured for azeotropic distillation. Toluene (8.65 wt, 10.0 vol) is added and the mixture stirred at 20 to 25° C. until a slurry is obtained (expected time 15 to 30 minutes). The reaction mixture is then heated to reflux over 30 to 60 minutes and maintained at reflux without collecting water, for 60 to 75 minutes.

The reaction mixture is then azeotropically dried by removal of water. This is expected to take 3 to 4 hours, after which time water should have stopped collecting. The reaction is sampled at roughly 30 minute intervals after 3 hours at reflux to determine the water content by KF. The reaction is complete when the KF of the reaction mixture is <0.1% (w/w). Additionally, the n-butanol content is checked by $^1$H NMR and if >1.5% (w/w) relative to the amine content, then toluene (0.865 wt, 1.0 vol) is added and the solution distilled at atmospheric pressure to remove ca 1 vol of distillate. This toluene addition/removal sequence is repeated as necessary to control the n-butanol level. If the KF result is greater than 0.1% (w/w), azeotrophic drying, with water removal, should be continued for an additional hour, and the solution resampled. The reaction mixture becomes almost homogenous after 3 hours although, caking of inorganic material on the walls of the reaction vessel may occur. At plant scale it is envisaged that the period of reflux will continue for 1 h after the time at which no water is observed in the condensate return and then the solution cooled for sampling. This is to enable safer sampling of the mixture.

When the reaction is complete, the mixture is cooled to 20 to 25° C. (typically over 60 to 75 minutes) maintaining nitrogen atmosphere throughout, aged for 1 to 2 hours and filtered under nitrogen into a suitable container, followed by a toluene line rinse (0.865 wt, 1.0 vol). The filtrate is weighed, analysed to determine the % (w/w) content of the free amine present in solution (expected value is ca 4 to 7% (w/w)) and is then carried through to the following step. The amine is very hygroscopic and should be protected from moisture and carbon dioxide at all times.

Stage 7A: Formation of the Acid Chloride

The input quantities are dependent on the amount of de-complexed amine available. The relative weights and volumes relate to the input stage 6 acid. It is recommended that ca 10% of the available de-complexed amine is retained in case a further charge is required to achieve reaction completion.

Stage 6 product (1.00 wt, 1.0 mol eq) is charged to the reaction vessel followed by THF (5.33 wt, 6.0 vol). The mixture is thoroughly stirred until a mobile slurry is obtained. DMF (0.01 wt, 0.01 vol) is added to the vessel and the resultant mixture stirred for 10 to 20 minutes. Thionyl chloride (0.608 wt, 0.373 vol, 1.22 mol eq) is then added ensuring the internal temperature in maintained at 20 to 25° C., followed by a line-rinse of THF (0.88 wt, 1.0 vol). The thionyl chloride addition is expected to take 20–40 minutes. Note: The reaction remains heterogeneous throughout the entire procedure. The reaction is monitored by IPC and is complete when level of starting acid is <2% area.

The reaction mixture is diluted with heptane (6.26 wt, 9.2 vol), cooled to 5 to 10° C. over 30 to 60 minutes, aged for 1–1.5 hours and then filtered under nitrogen. The filter cake is washed with heptane (2×2.72 wt, 2×4.0 vol) and then dried on the filter for 30 to 40 minutes under a blanket of nitrogen. The product is moisture sensitive, and must be kept under a nitrogen atmosphere at all times.

The crude product is charged to the reaction vessel followed by toluene (6.92 wt, 8.0 vol). Using concurrent addition/distillative removal of toluene (ca 8 vol) under reduced pressure whilst maintaining the reactor contents at ca 9 volumes and an internal temperature of 25 to 30° C., residual THF and heptane is removed. Distillation requires pressure of ca. 8–11 mmHg. The progress of distillation is monitored by IPC. The pass criterion is when $^1$H NMR shows THF and heptane each to be <1% (w/w) wrt toluene. The resultant slurry is then used directly in the subsequent stage 7 coupling.

The yield of the reaction is determined by analysis of the mother liquors to determine the amount of acid/acid chloride present and the balance is assumed to be as acid chloride in the filter-cake.

Stage 7C: Coupling to form the Stage 7 Product

The Relative Inputs are with Respect to the Amount of Acid Chloride (Stage 7A)

The acid chloride (1.00 wt, 1.0 mol eq) in toluene telescoped from the above reaction is thoroughly stirred under nitrogen at 20 to 25° C. A solution of the de-complexed amine in toluene (ca 10 to 15 vol; 0.57 wt contained based on the % (w/w) determination, 1.07 mol eq) is then added at a rate such that the internal temperature is maintained at 20 to 30° C. throughout. The addition is expected to take 30 to 60 minutes. A toluene line rinse (1.73 wt, 2.0 vol) is added to the reaction vessel. The reaction remains heterogeneous throughout the process. After ca 3 hours the reaction is sampled and its progress monitored by HPLC. The reaction is sampled at roughly 1 hourly intervals thereafter until IPC indicates complete reaction. The reaction is deemed to be complete when the diethylamide is <1% HPLC area. The reaction is expected to be complete after 4 hours.

The reaction is then filtered and the filter cake washed with toluene (2×4.32 wt, 2×5.0 vol) followed by heptane (2×3.4 wt, 2×5.0 vol) and then dried on the filter for 30 to 90 minutes. The filter cake is transferred to a vacuum oven and dried in vacuo at up to 45° C. until the levels of heptane and toluene are each <1% (w/w) and <2% (w/w) respectively by $^1$H NMR.

The overall yield from the Stage 6 acid is 75.6% th, 128.0% (w/w).

Stage Eight

The stage 7C salt (1.0 wt, 1.0 mol eq) is charged to the reaction vessel, followed by methanol (3.16 wt, 4.0 vol). The resulting suspension is stirred at 20–25° C. for 15–30 minutes to allow any large lumps of solid to break up. Sodium methoxide (25% (w/w) solution in methanol, 1.52 wt, 1.61 vol, 2.83 mol eq) is added, maintaining the internal temperature at 20–30° C. The addition is expected to take 20–30 minutes. The reaction mixture remains heterogeneous throughout. A line rinse of methanol (0.5 vol) is then added to the reaction mixture. The reaction mixture is heated to reflux and maintained at reflux until the reaction is complete (pass criterion is <0.5% starting material as reported by HPLC). The reaction is expected to take 60 minutes.

The reaction mixture is cooled to 20–25° C., and then water (11.0 vol.) is added maintaining the internal temperature at 20–30° C. The addition of water is expected to take 15–30 minutes. The resulting precipitate is aged for 50–70 minutes at 20–25° C., then cooled further to 5–10° C., aged for an additional 50–70 minutes and isolated by filtration. The filter cake is washed with cooled water (5–10° C., 2×3.0 vol) and the pH of the solid checked (expected range 7–9). If the pH is >9, further water washes are added. The solid is air-dried for 1–2 hours before being transferred to a vacuum oven and dried at up to 50° C. until the water content is <1% (w/w).

The yield for dried stage 8 material is 85.7% th, 69.6% (w/w).

Stage Nine

The stage 8 material (1.0 wt, 1.0 mol eq) is suspended in 96% ethanol B (3.95 wt, 5.0 vol) and stirred at 20–25° C. to obtain a mobile slurry (time expected 15–30 minutes). The reaction is heated to reflux; the material is not expected to go into solution below 45° C. After refluxing for 50–70 minutes, the solution is cooled to 60–65° C. and filtered through a pre-heated in-line filter using heated transfer lines, to remove insoluble material. The expected weight of insolubles is <0.01 wt. The stage 8 material is soluble in ethanol at up-to 40–45° C. The filter and lines are washed with hot ethanol (60–65° C., 0.79 wt, 1.0 vol).

The product containing solution is cooled to 20–25° C., and concentrated hydrochloric acid (0.4 wt, 0.34 vol) added, keeping the temperature between 20–30° C. The addition is expected to take 30–45 mins. Precipitation of the stage 9 product will occur after approximately 0.17–0.26 vol of acid has been added. Once the addition is complete, a line rinse of ethanol (0.79 wt, 1.0 vol) is added, and the slurry aged at 20–25° C. for 1–2 hours. The slurry is cooled to 0–5° C. and stirred for a further 1–2 hours before being filtered.

The solid is washed with cold ethanol (0–5° C., 0.79 wt, 1.0 vol), and then dried on the filter for 1–2 hours, and then at up-to 40° C. until the ethanol content is <0.1% (w/w) by $^1$H NMR. The solvent content is confirmed by GC headspace, and if <0.1% (w/w), the water content is determined by KF. If the water content is <8% (w/w), the product is re-hydrated until the water content is between 8–15% (w/w).

Yield of renzapride hydrochloride $H_2O$ is 66.4% th, 73.9%(w/w).

Scheme B

Alternative Synthetic Process

Stage 1

Preparation of ethyl 3-[1-(3-carbethoxy)-piperidinyl]propionate

Ethyl acrylate is added slowly to ethyl nipecotate with water cooling. The mixture is heated at about 55° for several hours to complete the reaction. Excess ethyl acrylate is distilled off in vacuo leaving the crude product, which is used directly in the next stage.

Yield is 162.0% (w/w).

Stage 2

Preparation of (±)-3-carbethoxy-1-azabicyclo]3.3.1] nonan-4-one hydrochloride

Sodium hydride is added carefully to toluene under nitrogen and the stirred mixture heated to reflux. The Stage 1 di-ester in toluene is added slowly, this reaction mixture is then refluxed for several hours. After cooling to about 5° C., water is added cautiously and the phases are then separated. Concentrated hydrochloric acid is added to the aqueous layer to pH 8.5, which is then extracted with dichloromethane. Concentrated hydrochloric acid is added to the combined organic solutions and the whole evaporated down to low volume in vacuo. The crude product concentrated in dichloromethane solution is used directly in Stage 3.

Yield is 90% (w/w).

Stage 3

Preparation of (±)-1-azabicyclo[3.3.1]nonan-4-one

The crude Stage 2 product is added to dilute hydrochloric acid with stirring and residual dichloromethane removed on gentle warming. The hours followed by cooling. Following basification with concentrated sodium hydroxide solution, the mixture is extracted several times with dichloromethane and the organic solutions evaporated in vacuo, to give the crude Stage 3 product which is used directly in Stage 4.

Yield is 56.0% (w/w).

Stage 4

Preparation of (±)-1-azabicyclo[3.3.1]nonan-4-one oxime hydrochloride

The crude Stage 3 product in ethanol is treated gradually with hydroxylamine hydrochloride, with cooling and stirring. The mixture is stirred for several hours at room temperature and crystalline material filtered off and washed with ethanol. Drying gives the Stage 4 product as a light brown crystalline solid.

Yield is 75% (w/w).

Stage 5

Preparation of [(±)-endo]-1-azabicyclo-[3.3.1] nonan-4-amine carbon dioxide complex The Stage 4 oxime hydrochloride is stirred and warmed in n-amyl alcohol under nitrogen. Sodium is added rapidly to maintain reflux and when all the sodium has dissolved, the mixture is cooled and a mixture of ice and water added. The amyl alcohol solution is separated from the aqueous layer, dried over anhydrous sodium sulphate, filtered and treated with solid carbon dioxide pellets. After standing for several hours, the Stage 5 product is filtered off, washed with n-amyl alcohol and ether and dried in vacuo.

Yield is 65% (w/w).

Stage A

Preparation of 4-acetamido-5-chloro-2-methoxybenzoic acid

Methyl 4-acetamido-5-chloro-2-methoxybenzoate is stirred with aqueous sodium hydroxide until complete solution is achieved. After filtration, concentrated hydrochloric acid is added, whereupon, the product precipitates out as a white solid which is filtered off, washed and dried. 4-Acetamido-5-chloro-2-methoxybenzoic acid is crystallised from isopropanol, filtered off, washed and dried.

Yield is 85% (w/w).

Stage B

Preparation of 4-amino-5-chloro-2-methoxybenzoic acid

Methyl 4-acetamido-5-chloro-2-methoxybenzoate is dissolved in ethanol and aqueous potassium hydroxide added. The solution is refluxed for a short time, cooled and concentrated hydrochloric acid added. The resulting precipitate is filtered off, washed with water and dried to give the title compound as a white solid.

Stage 6A

Preparation of [(±)-endo]-4-acetamido-5-chloro-2-methoxy-N-(1-azabicyclo[3.3.1]non-4-yl)-benzamide hydrochloride Oxalyl chloride is added to a suspension of 4-acetamido-5-chloro-2-methoxybenzoic acid (product of stage A) in dichloromethane followed immediately by dimethylformamide. The suspension is distilled in vacuo to give the acid chloride as a pale yellow solid which is dissolved in toluene.

Alternatively, thionyl chloride is added to 4-acetamido-5-chloro-2-methoyxbenzoic acid and the mixture stirred at room temperature for several minutes. The resulting solution is poured into petroleum spirit causing the acid chloride to precipitate as a white solid which is filtered, washed with petroleum spirit and dissolved in toluene.

In the meantime, a suspension of the Stage 5 product in toluene is heated to reflux and the hot solution filtered and cooled to about 50°. It is then added rapidly to a hot stirred solution of the acid chloride in toluene as prepared above, whereupon, the product starts to crystallise. After stirring for some time whilst cooling, the Stage 6A product is filtered off, washed with toluene and ether and dried.

Yield is 99% (w/w).

Stage 6B

Preparation of ((±)-endo]4-amino-5-chloro-2-methoxy-N-(1-azabicyclo[3.3.1]non-4-yl)-benzamide hydrochloride 4-Amino-5-chloro-2-methoxybenzoic acid (product of Stage B) is dissolved in dimethylformamide and triethylamine added. After cooling, ethyl chloroformate is added to the stirred solution followed by toluene and then a solution of the Stage 5 amine in toluene prepared as described in Stage 6A. After some time at room temperature, the solution is filtered giving a white solid which is washed with toluene and dried in vacuo. This crude material is crystallised twice with aqueous propan-1-ol and dried in vacuo, to give the Stage 6B product as a white solid. It can be hydrated if desired by keeping it in an atmosphere saturated with water vapour for several days.

Dichloromethane may be used as the solvent throughout instead of dimethylformamide and toluene.

Stage 7

Preparation of [(±)-endo]-4-amino-5-chloro-2-methoxy-N-(1-azabicyclo [3.3.1]non-4-yl)-benzamide The Stage 6A product is stirred in ethanol and an aqueous solution of potassium hydroxide added. The mixture is refluxed, then cooled to room temperature and the ethanol removed in vacuo to leave a slurry. Water is added and the mixture stirred for some time, then the white Stage 7 product is filtered off, washed with water and dried in vacuo.

Yield is 86% (w/w).

Stage 8

Preparation of [(±)-endo]4-amino-5-chloro-2-methoxy-N-(1-azabicyclo[3.3.1]non-4-yl)-benzamide hydrochloride The Stage 7 free base is dissolved in ethanol at reflux, filtered through celite and treated with a solution of hydrogen chloride in ethanol to precipitate the product. After cooling to room temperature with stirring, the Stage 8 product is filtered off, washed with ethanol and dried in vacuo. It can be hydrated if desired by keeping it in an atmosphere saturated with water vapour for several days.

Yield is 78% (w/w).

The invention claimed is:

1. A process for the preparation of compound (8)

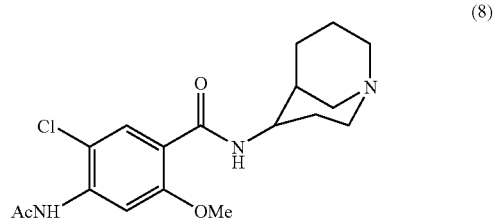

comprising 1) preparing acid chloride (13) from acid (11)

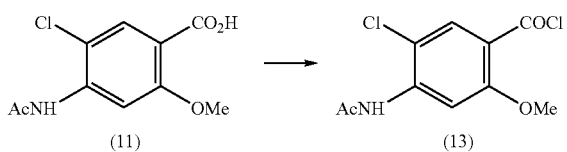

by reacting acid (11) with oxalyl chloride or thionyl chloride in dichloromethane, toluene, dimethylformamide (DMF) or tetrahydrofuran (THF)

2) reacting the acid chloride (13) in toluene with amine (14)

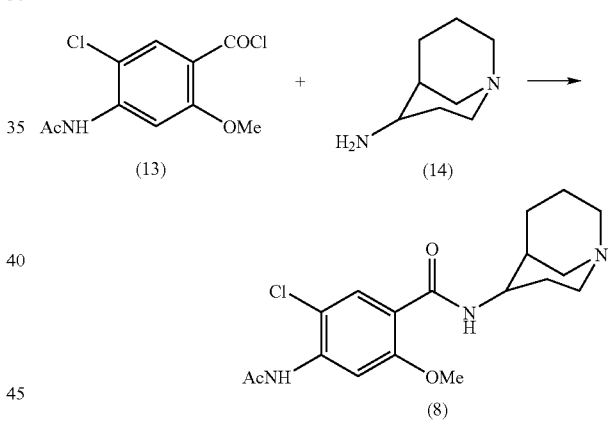

and isolating the product (8) therefrom.

2. A process as claimed in claim 1 wherein the preparation of the acid chloride (13) is carried out by reacting acid (11) with DMF and thionyl chloride in the presence of THF, wherein the DMF is added to the acid prior to the thionyl chloride and carrying out a solvent exchange with toluene prior to the reaction of the acid chloride with amine (14).

3. A process for the production of renzapride from acid 16 and amine (14)

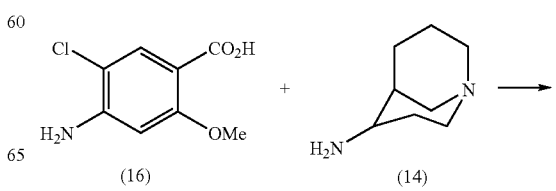

-continued

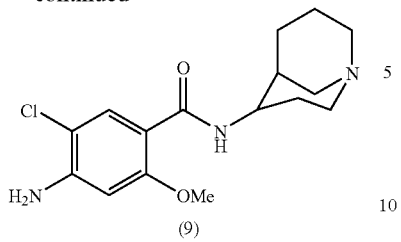

comprising reacting the acid (16) with DMF, triethylamine and ethyl chloroformate to form an in situ acidchloride, then reacting the in situ acid chloride with amine (14) in toluene.

4. A process for the preparation of renzapride from compound (8) claim 1 comprising preparing compound (9) from compound (8)

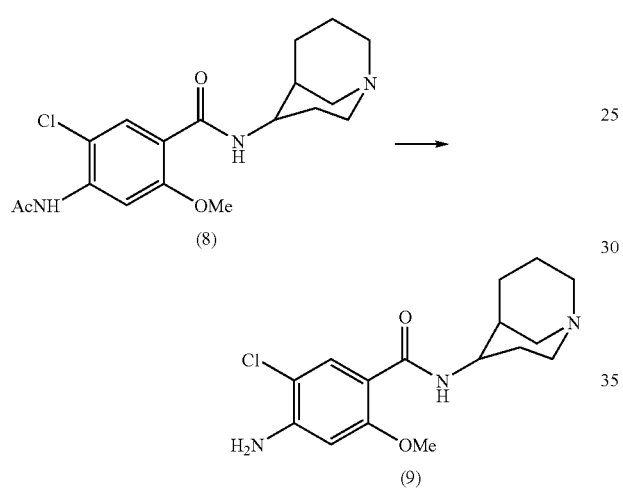

by refluxing compound 8 with a compound NaOR wherein R is hydrogen, methyl, or ethyl and methanol or ethanol.

5. A process according to claim 4 for the production of renzapride hydrochloride further comprising incubating compound (9)

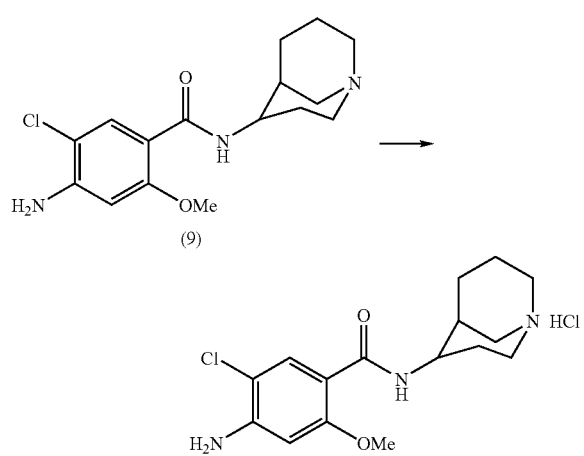

with ethanol and hydrochloric acid in ethanol and allowing the product to precipitate.

6. A process as claimed in claim 4 wherein the preparation of compound 9 is carried out by refluxing compound 8 in methanolic sodium methoxide.

7. A process for the preparation of compound (8):

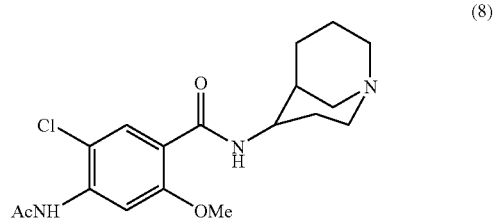

comprising the steps of:
a) forming amine (14):

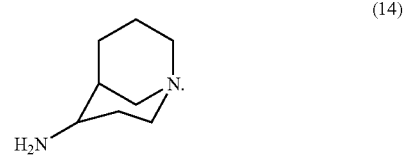

by forming compound (5) by:
1. preparing compound (3) from ethyl nipecotate

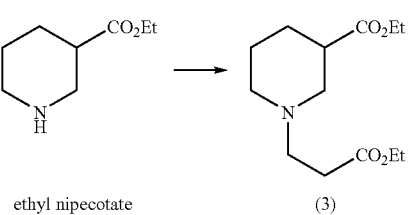

by reaction of ethyl nipecotate with ethyl acrylate:
2. preparing compound (4) from compound (3)

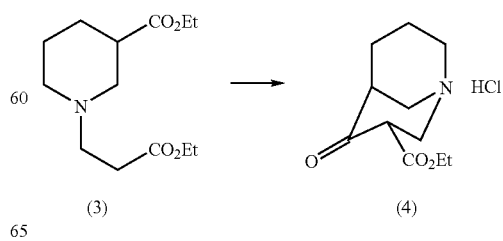

by reflux of compound (3) with base; and 3. preparing of compound (5) from compound (4)

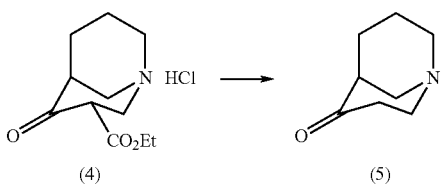

by reaction of compound (4) with aqueous HCl followed by sodium hydroxide;
and converting compound (5) to amine (14) comprising the steps of:
i. forming oxime (6) from compound (5):

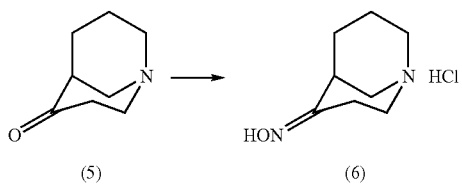

by the reverse addition of compound (5) in butanol to a slurry of hydroxylamine hydrochloride;
ii. converting compound (6) to compound (7):

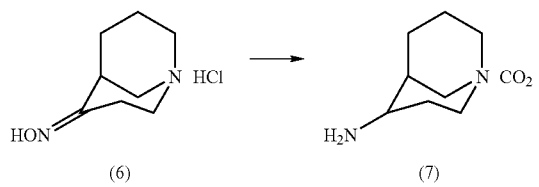

by reacting compound (6) with sodium followed by reaction with carbon dioxide characterised in that the reaction of compound (6) with sodium is carried out in butanol; and
iii. converting compound (7) to amine (14):

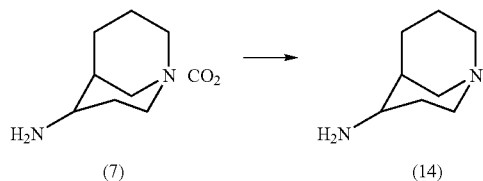

by decomplexation of the amine of compound (7) by reflux in toluene followed by azeotropic drying of the produced amine (14); and
b) reacting said amine (14) with acid (11)

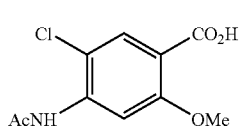

to afford compound (8).

8. A process for the preparation of compound (8) as claimed in claim 7 wherein acid (11) is prepared from compound (10):

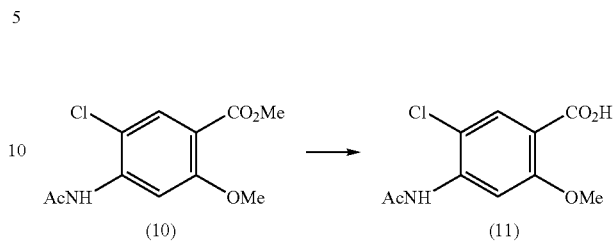

by the adding aqueous sodium hydroxide to a slurry of compound (10) in water, followed by precipitation of acid (11) by the addition of hydrochloric acid.

9. A process for the preparation of the hydrochloride salt of compound (9):

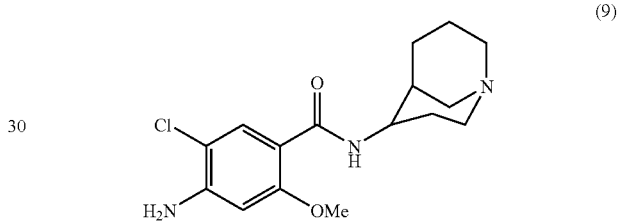

comprising converting compound (8), as prepared by the process of claim 7, into compound (9):

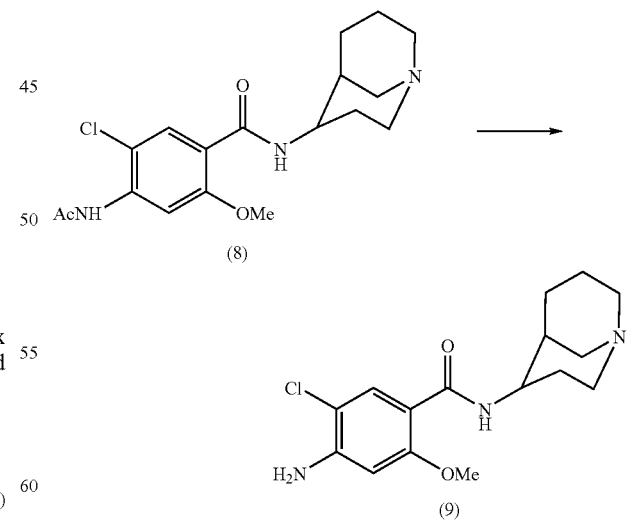

by refluxing compound (8) with a compound NaOR wherein R is hydrogen, methyl, or ethyl, and methanol or ethanol, or by refluxing compound (8) in methanolic sodium methoxide.

10. A process for the preparation of compound (9):
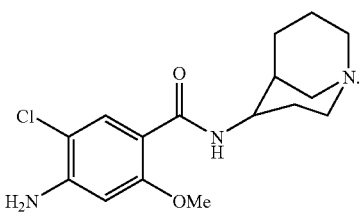
(9)
comprising the steps of:
a) forming amine (14) by the process of claim 7:
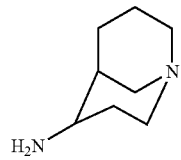
(14)
b) reacting acid (16)
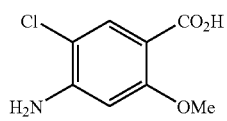
(16)
with DMF, triethylamine and ethyl chloroformate to form an in situ acid chloride thereof, and
(c) reacting the in situ acid chloride with amine (14) in toluene to prepare compound (9).
* * * * *

UNITED STATES PATENT AND TRADEMARK OFFICE
CERTIFICATE OF CORRECTION

PATENT NO.        : 7,189,852 B2
APPLICATION NO.   : 10/884842
DATED             : March 13, 2007
INVENTOR(S)       : Palmer et al.

It is certified that error appears in the above-identified patent and that said Letters Patent is hereby corrected as shown below:

Claim 4, Column 23, line 18:
　　after "compound (8)" and before "claim 1" please insert --according to--.

Signed and Sealed this

Sixth Day of November, 2007

JON W. DUDAS
*Director of the United States Patent and Trademark Office*